(12) United States Patent
Matsui et al.

(10) Patent No.: US 8,098,427 B2
(45) Date of Patent: Jan. 17, 2012

(54) MICROSCOPIC INSEMINATION VIEWING METHOD

(75) Inventors: Kumiko Matsui, Yokohama (JP); Katsuya Watanabe, Yokohama (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 12/840,248

(22) Filed: Jul. 20, 2010

(65) Prior Publication Data

US 2010/0284065 A1    Nov. 11, 2010

Related U.S. Application Data

(63) Continuation of application No. PCT/JP2009/050555, filed on Jan. 16, 2009.

(30) Foreign Application Priority Data

Jan. 23, 2008    (JP) ................................ 2008-012823

(51) Int. Cl.
    *G02B 21/00*       (2006.01)
(52) U.S. Cl. ........... 359/370; 359/381; 359/900; 600/35
(58) Field of Classification Search ........................ None
See application file for complete search history.

(56) References Cited

U.S. PATENT DOCUMENTS

| | | | |
|---|---|---|---|
| 4,200,353 A | | 4/1980 | Hoffman |
| 4,920,053 A | * | 4/1990 | Inoue et al. ................. 435/30 |
| H1763 H | | 12/1998 | Mizusawa |
| 2003/0039953 A1 | * | 2/2003 | Bartoov ........................ 435/4 |

FOREIGN PATENT DOCUMENTS

| | | |
|---|---|---|
| JP | 51-128548 A | 11/1976 |
| JP | 08-136816 A | 5/1996 |
| JP | 9-15504 A | 1/1997 |
| JP | 9-236753 A | 9/1997 |
| JP | 2000-155266 A | 6/2000 |
| JP | 2000-241710 A | 9/2000 |
| JP | 2001-356278 A | 12/2001 |
| JP | 2003-75724 A | 3/2003 |
| JP | 3415294 B2 | 4/2003 |
| JP | 2003-131139 A | 5/2003 |
| JP | 3456252 B2 | 8/2003 |
| JP | 2006-184929 A | 7/2006 |

OTHER PUBLICATIONS

A. Berkovitz, F. Eltes, A. Ellenbogen, S. Peer, D. Feldberg, B. Bartoov, 'Does the presence of nuclear vacuoles in human sperm selected for ICSI affect pregnancy outcome?', Hum. Reprod., vol. 21, No. 7, pp. 1787-1790, 2006.*

(Continued)

*Primary Examiner* — Arnel C Lavarias
(74) *Attorney, Agent, or Firm* — Miles & Stockbridge P.C.

(57) ABSTRACT

A microscope system includes a transmission illumination optical system having a light source and a condenser lens; a first dry objective having a magnification of from 20 or higher to 40 or lower and capable of viewing by at least one of a differential interference viewing method and a modulation contrast viewing method; and a second dry objective having a magnification of from 60 or higher to 100 or lower and capable of viewing by a differential interference viewing method; the first objective and the second objective being exchangeable.

4 Claims, 6 Drawing Sheets

OTHER PUBLICATIONS

A. Van Steirteghem, Z. Nagy, H. Joris, J. Liu, C. Staessen, J. Smitz, A. Wisanto, P. Devroey, 'High fertilization and implantation rates after intracytoplasmic sperm injection', Hum. Reprod., vol. 8, No. 7, pp. 1061-1066, 1993.*

B. Bartoov, A. Berkovitz, F. Eltes, A. Kogosovsky, A. Yagoda, H. Lederman, S. Artzi, M. Gross, Y. Barak, 'Pregnancy rates are higher with intracytoplasmic morphologically selected sperm injection than with conventional intracytoplasmic injection', Fert. Ster., vol. 80, No. 6, pp. 1413-1419, Dec. 2003.*

A. Berkovitz, F. Eltes, H. Lederman, S. Peer, A. Ellenbogen, B. Feldberg, B. Bartoov, 'How to improve IVF-ICSI outcome by sperm selection', Reprod. BioMed. Online, vol. 12, No. 5, pp. 634-638, 2006.*

B. Bartoov, A. Berkovitz, F. Eltes, A. Kogosowski, Y. Menezo, Y. Barak, 'Real-time fine morphology of motile human sperm cells is associated with IVF-ICSI outcome', J. Andrology, vol. 23, No. 1, pp. 1-8, Jan. 2002.*

P. Sutovsky, J. Ramalho-Santos, R. Moreno, R. Oko, L. Hewitson, G. Schatten, 'On-stage selection of single round spermatids using a vital, mitochondrion-specific fluorescent probe MitoTrackerTM and high resolution differential interference contrast microscopy', Hum. Reprod., vol. 14, No. 9, pp. 2301-2312, 1999.*

* cited by examiner

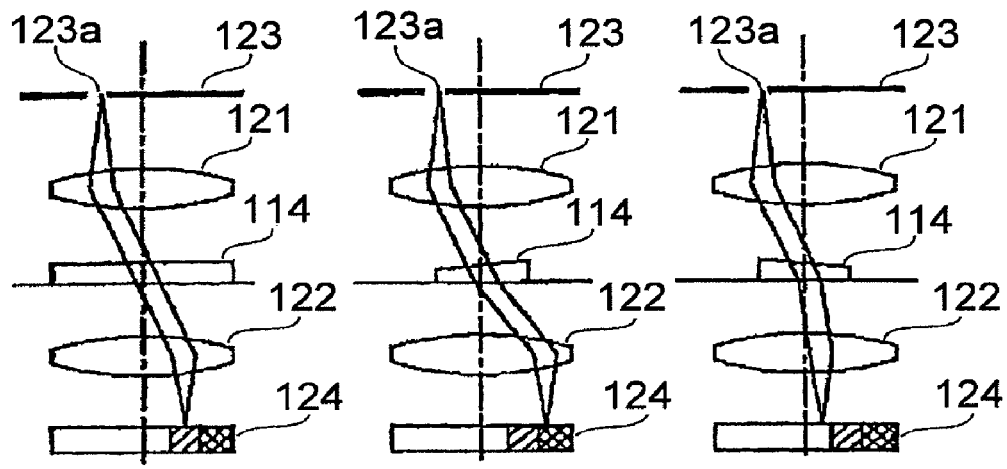
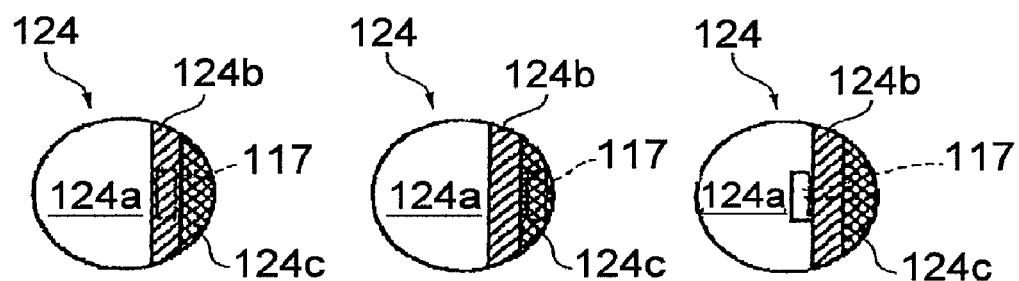

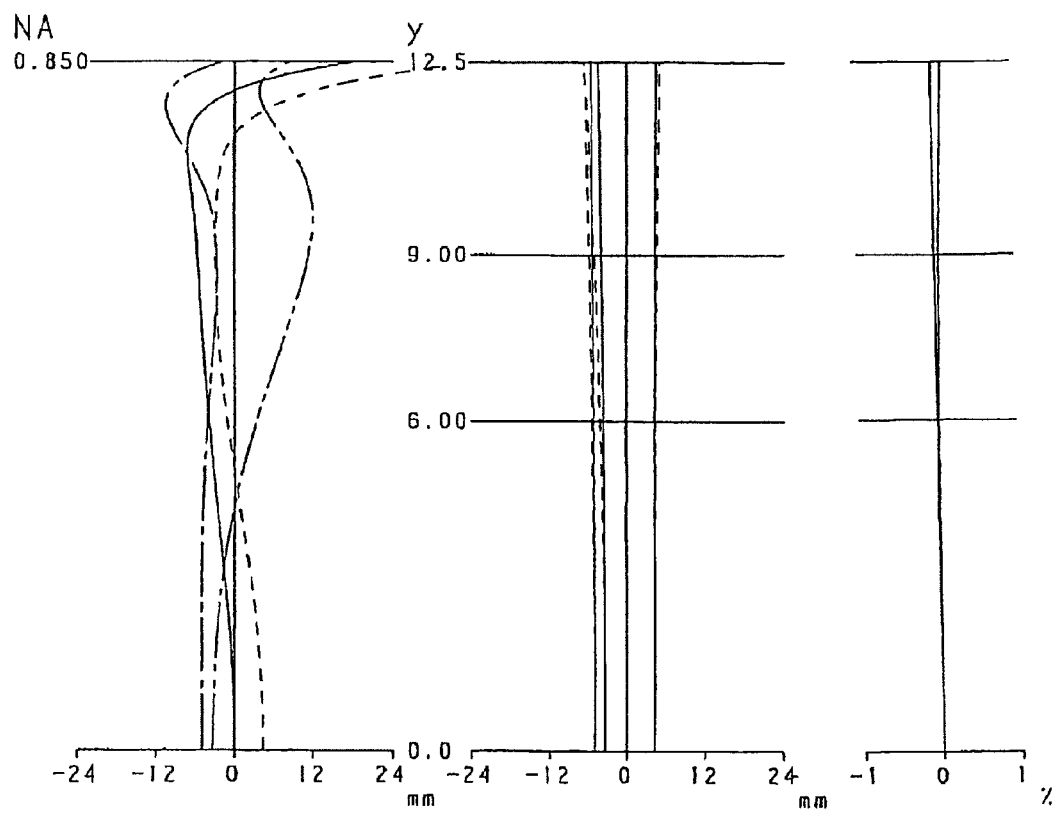

MICROSCOPIC INSEMINATION VIEWING METHOD

This is a continuation of PCT International Application No. PCT/JP2009/050555, filed on Jan. 16, 2009, which is hereby incorporated by reference. This application also claims the benefit of Japanese Patent Application No. 2008-012823, filed in Japan on Jan. 23, 2008, which is hereby incorporated by reference.

TECHNICAL FIELD

The present invention relates to a microscope system for use with micro-insemination, the system being capable of viewing using a differential interference viewing method and a modulation contrast viewing method.

TECHNICAL BACKGROUND

At present, ICSI (intra-cytoplasmic sperm injection) is widely used as a micro-insemination method. In micro-insemination, a sperm is selected using a modulation contrast viewing method (see Patent Document 1, for example), and a sperm having satisfactory motility and morphology is injected into an ovum. However, recent advances in IVF (in-vitro fertilization) research have shown statistically that such factors as the presence, size, and number of vacuoles in the sperm head are significantly related to the IVF success rate, but vacuoles in the sperm head are difficult to view by the modulation contrast viewing method used for conventional ICSI. Therefore, a microscope system has been proposed for enabling IMSI (intra-cytoplasmic morphologically selected sperm injection, which is a micro-insemination method in which a sperm is selected under high magnification), in which micro-insemination is performed after selection by detailed viewing of the inside of the sperm head, to be performed in addition to the conventional ICSI. For example, a configuration is adopted in which the modulation contrast viewing method used in ICSI is employed jointly with a differential interference viewing method (see Patent Documents 2 and 3, for example) through a high-magnification objective that is used in IMSI.

Patent Document 1: Japanese Laid-open Patent Publication No. S51-128548
Patent Document 2: Japanese Patent No. 3456252
Patent Document 3: Japanese Patent No. 3415294

DISCLOSURE OF THE INVENTION

Problems to be Solved by the Invention

In the differential interference viewing method used in the micro-insemination described above and well as in other fields of biological microscopy, structures must be observable in as much detail as possible, and an immersion objective having a high numerical aperture (NA) has generally been used as a high-magnification lens. As a result, in the conventional microscope system, an immersion-type lens is used as a high-magnification objective, and a dry-type lens is used as a medium-low-magnification objective, and during the switch to the dry-type medium-low-magnification objective for ICSI viewing after IMSI viewing through the immersion-type high-magnification objective, the immersion liquid significantly interferes with the workability of IVF. In order to overcome this problem, a system has been proposed in which an immersion objective is used as the medium-low-magnification objective for ICSI viewing, as with the high-magnification objective. In this system, however, the viscosity of the immersion liquid causes the sample (usually a dish) to move when immersion objectives are used exchangeably, the sperm selected using the high-magnification objective may move out of view, and bubbles and the like are prone to be introduced into the immersion liquid. These problems can make ICSI viewing extremely difficult after the objectives are exchanged.

The present invention was developed in view of such problems, and an object of the present invention is to provide a microscope system suitable for IMSI/ICSI, whereby the sequence of operations for micro-insemination can be accurately and rapidly performed while maintaining resolving power, by viewing and selecting a sperm by a differential interference viewing method using a dry-type high-magnification objective, then injecting the selected sperm into an ovum by a differential interference viewing method or a modulation contrast viewing method using an exchanged low-magnification objective, which is also a dry-type objective.

Means to Solve the Problems

In order to achieve such objects as those described above, the present invention is a microscope system suitable for micro-insemination, and is characterized in comprising a transmission illumination optical system having a light source and a condenser lens; a first dry objective having a magnification of from 20 or higher to 40 or lower and capable of viewing by at least one of a differential interference viewing method and a modulation contrast viewing method; and a second dry objective having a magnification of from 60 or higher to 100 or lower and capable of viewing by a differential interference viewing method; the first objective and the second objective being exchangeable.

Advantageous Effects of the Invention

As described above, according to the present invention, a microscope system suitable for micro-insemination can be provided whereby the sequence of operations in micro-insemination can be rapidly and accurately performed with satisfactory workability while the appropriate resolving power is maintained.

BRIEF DESCRIPTION OF THE DRAWINGS

FIG. 2 is a view showing the underlying principle of the modulation contrast viewing method, which is another viewing method used in the microscope system of the present embodiment;

FIG. 3 is a view showing the positional relationship between the aperture image and the modulator in the modulation contrast viewing method according to the present embodiment, wherein FIG. 3A, FIG. 3B, and FIG. 3C correspond to FIG. 2A, FIG. 2B, and FIG. 2C;

FIG. 4A is a view showing an example of the shape of the sample, and FIG. 4B is a view showing the shading that appears corresponding to the sample in the modulation contrast viewing method according to the present embodiment;

FIG. 8 shows several aberration diagrams for the second objective according to the first example, wherein FIG. 8A is a spherical aberration diagram, FIG. 8B is an astigmatism diagram, and FIG. 8C is a distortion diagram.

Figure 1:
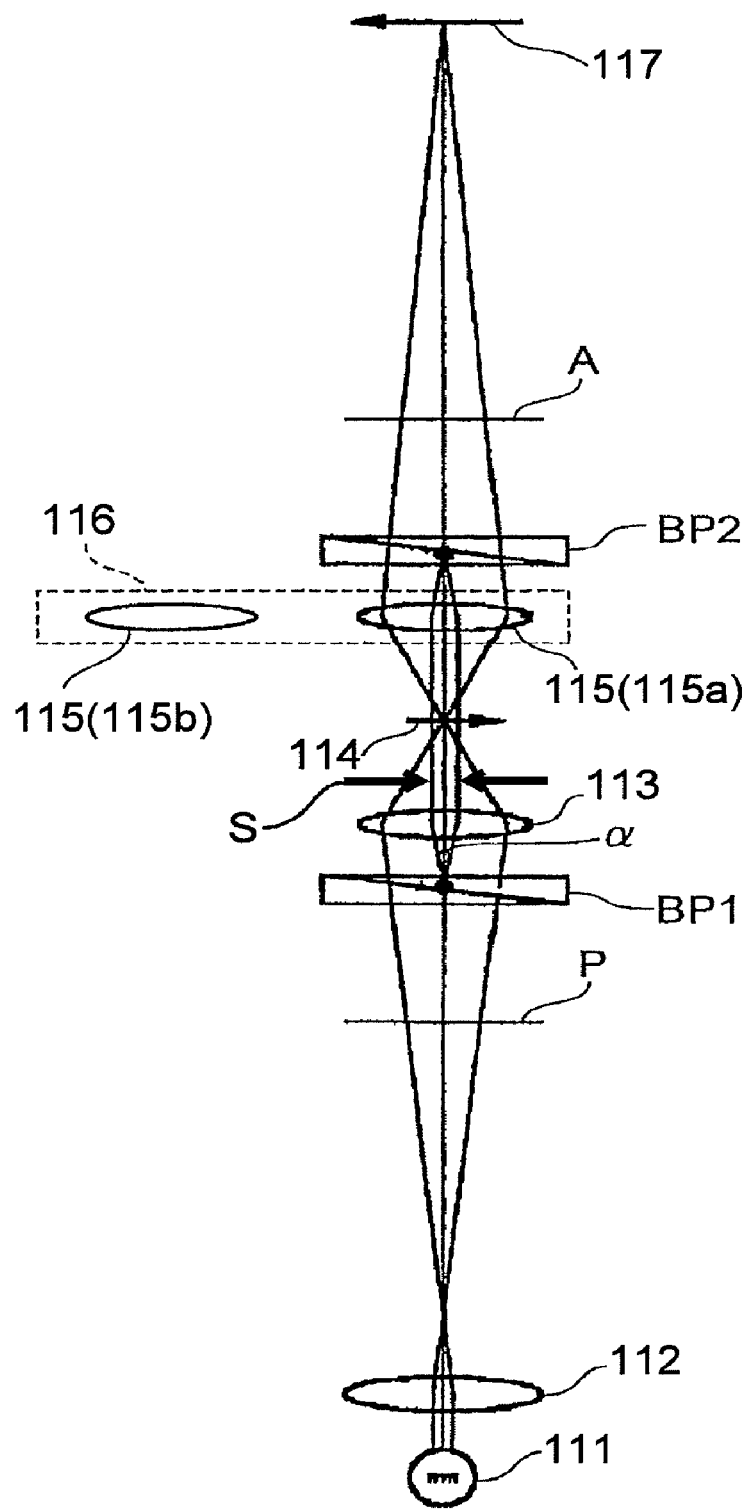
FIG. 1 is a schematic sectional view showing the microscope system utilizing a differential interference viewing method according to the present embodiment.

EXPLANATION OF NUMERALS AND CHARACTERS 111 light source (transmission illumination optical system)
112 collector lens
113 condenser lens (transmission illumination optical system)
114 sample
115 objective
115a medium-magnification objective (first objective) (capable of viewing by a differential interference viewing method)
115b high-magnification objective (second objective)
116 turret
BP1 illumination-side birefringent optical member
BP2 imaging-side birefringent optical member
P polarizer
A analyzer
122 medium-magnification objective (first objective) (capable of viewing by a modulation contrast viewing method)
123 aperture plate
123a rectangular aperture
124 modulator

DESCRIPTION OF THE PREFERRED EMBODIMENTS

Preferred embodiments will be described with reference to the drawings. FIG. 1 is a schematic sectional view showing a microscope system suitable primarily for micro-insemination, according to the present embodiment. The microscope system according to the present embodiment is suitable for IMSI (intra-cytoplasmic morphologically selected sperm injection, which is a micro-insemination method in which a sperm is selected under high magnification) and ICSI (intra-cytoplasmic sperm injection), and as shown in FIG. 1, the microscope system has a transmission illumination optical system composed of a light source 111 and a condenser lens 113; a collector lens 112; a sample 114; an objective 115; a turret 116; an illumination-side birefringent optical member BP1; an imaging-side birefringent optical member BP2; a polarizer P; and an analyzer A.

In FIG. 1, the illuminating light from the light source 111 is incident on the polarizer P after being collected by the collector lens 112, and is converted to linearly polarized light. The illumination-side birefringent optical member BP1 and the condenser lens 113 for irradiating the illuminating light on the sample 114 are provided in order from the light source 111 side in the optical path between the polarizer P and the sample 114. The linearly polarized light emitted from the polarizer P is incident on the illumination-side birefringent optical member BP1 and split by birefringence into two linearly polarized light components having mutually orthogonal directions of vibration, and the linearly polarized light components are incident on the condenser lens 113. The two rays split by the illumination-side birefringent optical member BP1 travel at a small separation angle α, are converted to parallel rays separated from each other at a small shear distance S by the collecting effect of the condenser lens 113, and illuminate the sample 114. The two rays transmitted at slightly separated positions on the sample 114 are incident on the imaging-side birefringent optical member BP2 via the objective 115 and combined by the birefringent effect of the imaging-side birefringent optical member BP2 so as to travel on the same optical path. The combined rays are incident on the analyzer A, the analyzer A extracts only the components of the mutually orthogonal linearly polarized light that are vibrating in the same direction, and these components interfere. As a result, a magnified image (interference image 117) on the image plane is formed by an interference fringe that forms according to the phase difference imparted between the two light rays as the rays pass through the sample 114 in slightly different positions. An observer can view the magnified image 117 through an eyepiece optical system not shown in the drawing.

When the sample 114 is planar and homogeneous, (since there is no phase difference between the two split rays of light,) the magnified image 117 is an image that has a uniform intensity distribution and is devoid of contrast. On the other hand, when the sample 114 is heterogeneous and has gradients and level differences, (since there is a phase difference between the two split rays of light,) contrasts occur in the magnified image 117 in portions where the refractive index varies, or in portions that correspond to gradients and level differences. The refractive index variations or the gradients and level differences are thereby made visible, and the sample 114 can be viewed at magnification.

The objective 115 is composed of a first objective 115a having a magnification of from 20 or higher to 40 or lower (hereinafter referred to as a dry-type medium-magnification objective or a medium-magnification objective), and a second objective 115b having a magnification of from 60 or higher to 100 or lower that is capable of contrast viewing by a differential interference viewing method (hereinafter referred to as a dry-type high-magnification objective or a high-magnification objective), and the medium-magnification objective 115a and the high-magnification objective 115b are configured so as to be exchangeable with the aid of a turret 116 or the like.

The first objective 115a is preferably capable of viewing by at least one of the abovementioned differential interference viewing method or modulation contrast viewing method. The underlying principles of the modulation contrast viewing method will be briefly described using FIGS. 2 through 4. In the drawings, the reference numeral 121 refers to a condenser lens, 114 refers to a sample, 122 refers to an objective, 123 refers to an aperture plate, and 124 refers to a disk-shaped modulator. The aperture plate 123 has a rectangular aperture 123a positioned at a distance from the center, in the focal position on the light source side of the condenser lens 121. The modulator 124 is provided in a position substantially conjugate to the aperture plate 123, and a 100% transmittance region 124a that may include the image of the aperture 123a, a region 124b of 15% transmittance, for example, and a 0% transmittance region 124c are formed in the stated order adjacent to each other in the modulator 124.

In this optical system, since the rectangular aperture 123a is disposed in an eccentric position with respect to the optical axis, light that is incident on the condenser lens 121 is emitted so as to illuminate the sample 114 at an oblique angle. When the transparent sample 114 is planar as shown in FIG. 2A, the flux of light passing through the sample 114 is focused in the region 124b of the modulator 124 by the objective 122, and an aperture image 117 is formed in the region 124b, as shown in FIG. 3A. When the surface of the sample 114 is inclined so as to rise to the right, as shown in FIG. 2B, the flux of light that passes through the sample 114 is refracted to the right and focused in the region 124c of the modulator 124, and the aperture image 117 is formed in the region 124c, as shown in FIG. 3B. When the surface of the sample 114 is inclined so as to rise to the left, as shown in FIG. 2C, the flux of light that passes through the sample 114 is refracted to the left and focused in the region 124a of the modulator 124, and the aperture image 117 is formed in the region 124a, as shown in FIG. 3C.

As is apparent from this description, when the sample 114 is a colorless transparent body having flat surfaces and inclined surfaces such as shown in FIG. 4A, the viewed image is such that the flat portions appear gray and the inclined portions appear black or white such as shown in FIG. 4B. The modulation contrast viewing method thus enables even a colorless transparent sample to be viewed as a three-dimensional image with shading, through the effects of focal illumination and regions of the modulator 124 having different transmittances.

In this microscope system, when the medium-magnification objective 115a that is capable of contrast viewing by a modulation contrast viewing method is used, a change is made to the illumination-side birefringent optical member BP1, imaging-side birefringent optical member BP2, polarizer P, and analyzer A, which are members used for viewing by the differential interference viewing method described above; and the aperture plate 123 and the modulator 124 are placed between the light source 111 and the condenser lens 113 (in the stated order from the light source 111).

In the microscope system according to the present embodiment, the following Conditional Expressions (1) and (2) are preferably satisfied, where NA is the numerical aperture of the dry-type second objective (high-magnification objective), f is the focal distance thereof, and WD is the working distance thereof.

$$0.78 \leq NA < 1.0 \quad (1)$$

$$f/3 \leq WD < 2f \quad (2)$$

In viewing by the differential interference viewing method using the second objective, the following Conditional Expression (3) is preferably satisfied, where S is the shear distance in the object plane, NA is the numerical aperture of the second objective, and A is the wavelength of the viewed light.

$$0.3\lambda/NA \leq S \leq 0.61\lambda/NA \quad (3)$$

In the past, resolving ability was considered critical in viewing by the differential interference viewing method using a high-magnification (60 or higher and 100 or lower), high numerical aperture immersion objective in the field of biological microscopy, and intervention using video enhancement or other image processing was assumed. However, during IMSI or other micro-insemination, visual observation is consistently used in order to rapidly and accurately perform the sequence of operations whereby a more satisfactory sperm is selected from a wide range of (numerous) sperm under high magnification, and the selected sperm is then injected into an ovum under medium magnification. There is accordingly a need for visually adequate contrast, but optimum conditions have not yet been presented for an objective capable of viewing by a differential interference viewing method that would satisfy the need for adequate contrast. The optimum Conditional Expressions (1) through (3) have therefore been derived for the second objective (high-magnification objective) for enabling viewing by the differential interference viewing method in the present microscope system. There follows a description of Conditional Expressions (1) through (3) in the stated order.

Conditional Expression (1) for specifying the range of appropriate numerical apertures NA of the high-magnification objective will first be described. In the present microscope system, the head portion of a sperm, an image of which is viewed in the present microscope system, is about 4 to 5 µm in size, and it has been confirmed that one to ten vacuoles of various sizes are scattered through the head portion in a single focal plane. Consequently, the ability to see and identify details about 0.4 to 0.5 µm in size with good contrast is understood to be adequate for IMSI applications.

Figure 5:
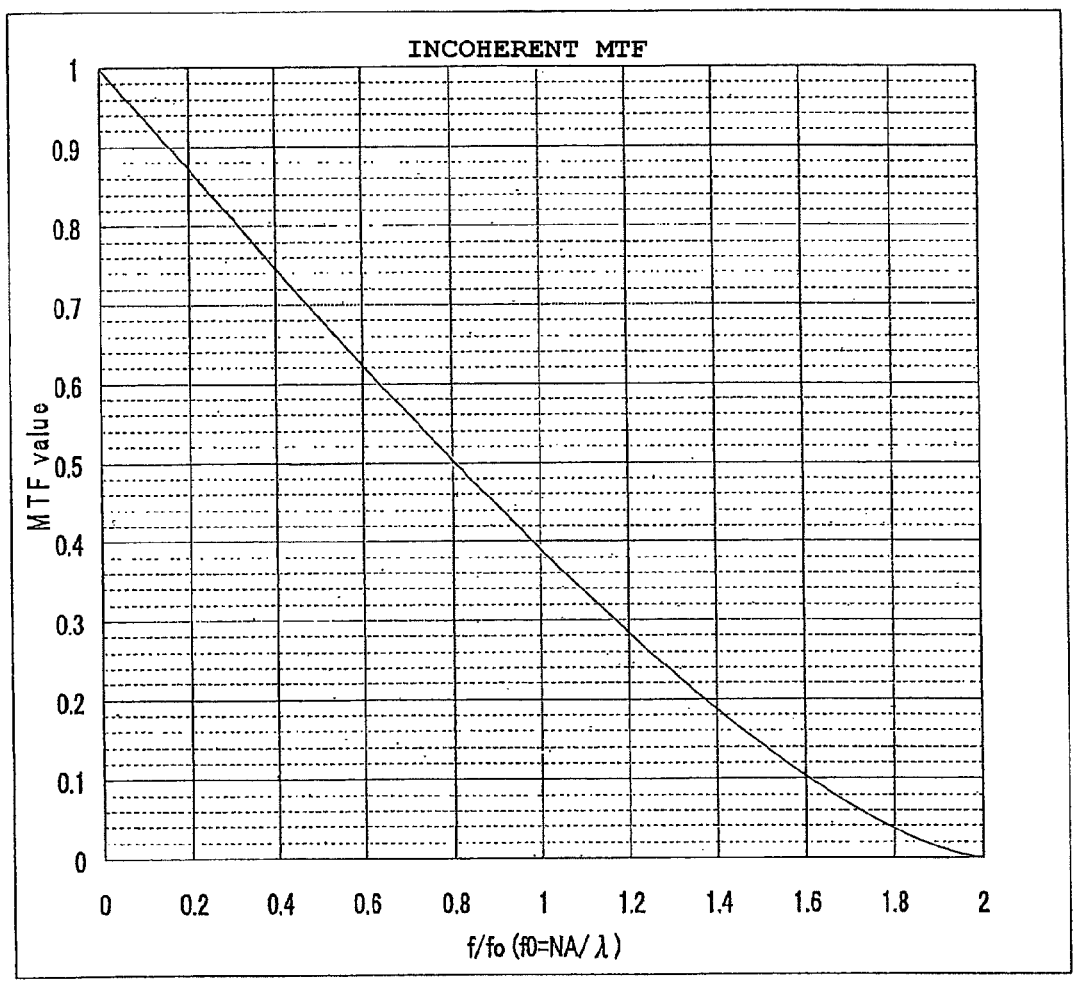
FIG. 5 is a view showing the MTF curve of the incoherent optical system according to the present embodiment.

FIG. 5 shows the MTF curve (i.e., the relationship between contrast on the vertical axis and the resolving power of the optical system on the horizontal axis) of the incoherent optical system commonly used in a microscope optical system. On the horizontal axis f/f0 of FIG. 5, the spatial frequency f is normalized so that $f0=NA/\lambda$, where f is the spatial frequency, NA is the numerical aperture of the objective, and $\lambda$ is the wavelength of the viewed light. The relationship to the horizontal resolving power RES corresponding to the spatial frequency f is indicated by Equation (4), where RES is the horizontal resolving power of the microscope optical system.

$$RES=1/f=\{1/(f/f0)\}\times\{\lambda/NA\} \quad (4)$$

The maximum value of 2.0 for the horizontal axis f/f0 shown in FIG. 5 corresponds to the maximum resolving power RES(max) of the microscope optical system. Therefore, by substituting f/f0=2.0 in Equation (4), Equation (5) is obtained, in which the maximum resolving power RES(max) of the microscope optical system is indicated. An image is difficult to see when there is no additional margin beyond the numerical aperture NA that corresponds to the maximum resolving power RES(max) specified by Conditional Expression (5).

$$RES(max)=\{1/2.0\}\times\{\lambda/NA\}=0.5\lambda/NA \quad (5)$$

It is known that the human eye generally has difficulty distinguishing contrast values of 0.1 or lower, and that visibility is satisfactory when the contrast value is 0.2 or higher. In FIG. 5, since the spatial frequency f/f0 at which the contrast value is 0.1 is near 1.6, Equation (6) must be satisfied by substituting these values into Equation (4) in order for the horizontal resolving power RES to be 0.4 µm (the size of a vacuole in the sperm head as the viewed image).

$$RES=\{1/1.6\}\times\{\lambda/NA\}=0.4 \quad (6)$$

Since visual observation is assumed in IMSI and ICSI, which are the applications for which the present microscope system is used, the central wavelength $\lambda$ during viewing is preferably in the vicinity of 500 nm to 550 nm when visibility to the eye is considered. The reason for this is that 500 nm and 550 nm are visibility peaks for dark locations and bright locations, respectively. When the central wavelength $\lambda$ of 500 nm=0.5 µm for viewing is substituted into Equation (6), Equation (7) below is obtained as the lower limit of the numerical aperture NA required for the high-magnification objective.

$$NA=\{1/1.6\}\times 0.5\,[\mu m]/0.4\,[\mu m]=0.78 \quad (7)$$

Since the spatial frequency f/f0 at which the contrast value is 0.2, which is considered to produce good visibility, is near 1.4 according to FIG. 5, a more preferred lower limit for the numerical aperture NA is obtained from Equation (8) by substituting into Equation (6) in the manner described above.

$$NA=\{1/1.4\} \times 0.5 \text{ [µm]}/0.4 \text{ [µm]}=0.89 \quad (8)$$

The numerical aperture NA is indicated by $NA = n \cdot \sin(\phi/2)$, where n is the refractive index of the medium between the objective and the sample, and $\phi$ is the aperture angle, and the medium in the present embodiment is air (refractive index n=1). Therefore, the maximum numerical aperture NA is 1.

In summary, in the microscope system of the present embodiment, the range of the numerical aperture NA of the high-magnification objective preferred for enabling visual observation with good contrast is expressed by Conditional Expression (1), i.e., $0.78 \leq NA < 1.0$. The range of the numerical aperture NA of the high-magnification objective is more preferably $0.89 \leq NA < 1.0$, according to Conditional Expression (8).

Conditional Expression (2) will next be described, which specifies the appropriate range of the working distance WD in the high-magnification objective. In the conventional microscope system, a large working distance is generally difficult to obtain with the high-numerical-aperture immersion objective used as the high-magnification objective. Therefore, when such an objective is used in ICSI viewing or IMSI viewing, which require that the sample be kept at 37° C. by an insulating device or the like during working, the insulation device and the distal end of the objective are prone to interfere during the switch from high magnification to the medium-magnification objective. Since a large working distance cannot be obtained, only the area immediately below the cover glass can be viewed by the high-numerical-aperture immersion objective, and sperm that are positioned at a distance from the cover glass cannot be targeted for selection. Therefore, a dry-type lens is used as the high-magnification objective in the present microscope system, and the condition of having the large working distance WD indicated by Conditional Expression (2) is thereby provided in addition to the condition of the numerical aperture NA indicated by Conditional Expression (1).

One factor that determines the working distance is the magnification of the objective. In an infinity-corrected optical system, the magnification of the objective is determined by the ratio of the focal distances of the imaging lens and the objective (in a high-magnification objective having a magnification of from 60 or higher to 100 or lower such as in the present embodiment, when the focal distance of the imaging lens is 200 mm, for example, the focal distance of the objective is 2.00 to 3.33 m), and the focal distance shortens as the magnification increases. In general, since the working distance is proportional to the focal distance of the objective, the working distance decreases as the magnification of the objective increases. Another factor that determines the working distance is the numerical aperture. When the size of the numerical aperture is the same, a longer working distance corresponds to a greater height of the light rays at the first lens surface (surface of the lens on the object side) of the objective, and aberration becomes more difficult to correct.

In other words, since increasing the working distance of the objective is incompatible with increasing the magnification and numerical aperture thereof, high-magnification objectives used in conventional microscope systems are polarized between those with an emphasis on working distance and those with an emphasis on magnification and numerical aperture. Specifically, magnification 60/numerical aperture 0.7/working distance 2 mm are typical specifications for working-distance-oriented objectives; and magnification 100/numerical aperture 1.4/working distance 0.11 nm are typical specifications for magnification/numerical-aperture-oriented objectives. However, when viewing IMSI is the intended application, the numerical aperture NA does not necessarily exceed 1, as indicated by Conditional Expression (1), and increasing the working distance by a corresponding amount leads to enhanced working efficiency.

Therefore, Conditional Expression (2), i.e., $f/3 \leq WD < 2f$, is preferably satisfied in the present embodiment, where NA is the numerical aperture of the high-magnification objective (second objective), f is the focal distance, and WD is the working distance. When Conditional Expression (2) is below the lower limit value, there is increased risk of such problems as interference between the distal end of the objective and the insulation device during exchanging of the objectives. When Conditional Expression (2) exceeds the upper limit value, the light rays at the first lens surface of the objective are too high, and it is difficult to ensure the numerical aperture NA specified by Conditional Expression (1).

Figure 6:
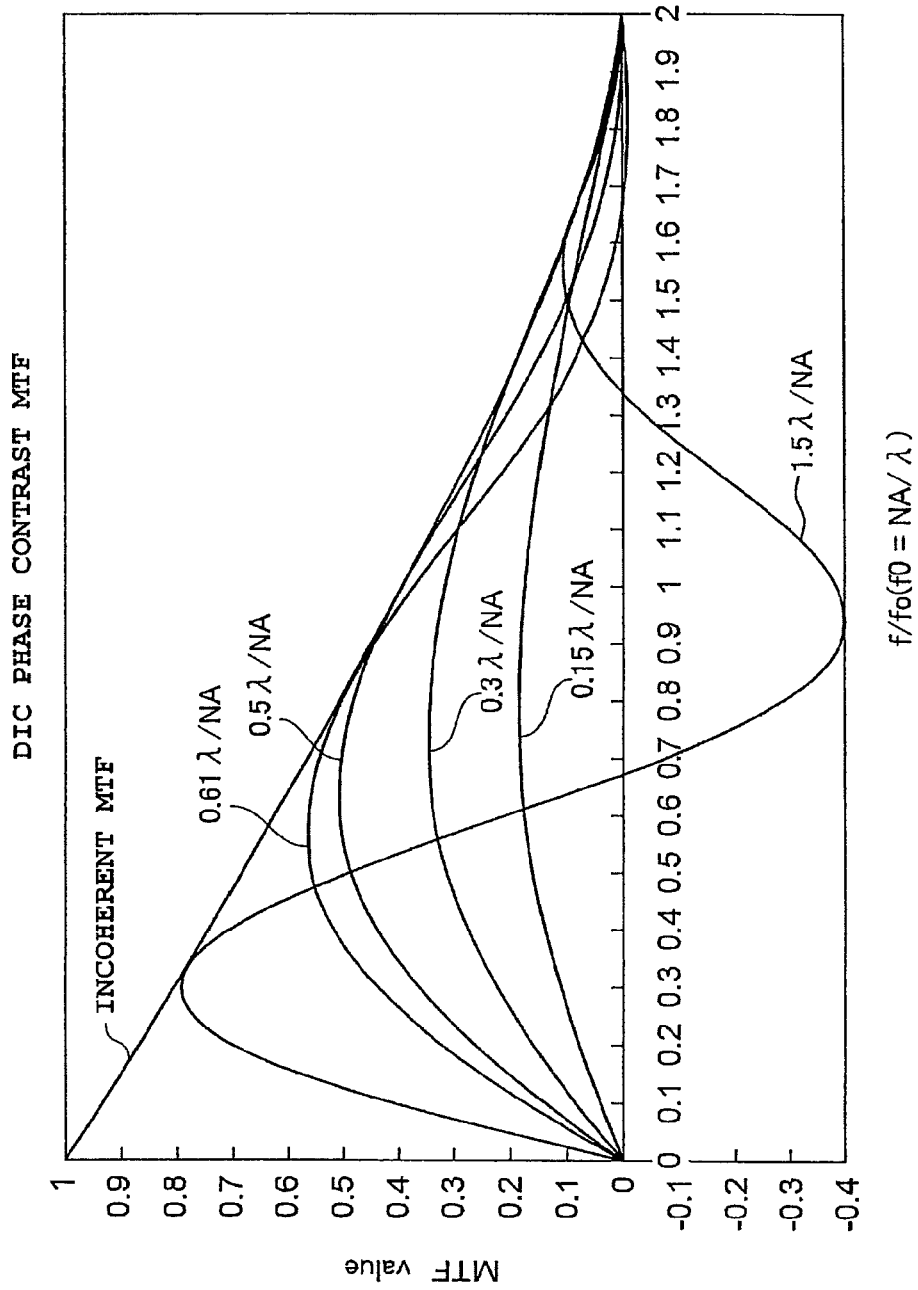
FIG. 6 is a view showing the contrast MTF curves of phase samples in the differential interference viewing method according to the present embodiment.

Conditional Expression (3) will next be described. Conditional Expression (3) specifies the optimum range of the shear distance S in the differential interference viewing method. FIG. 6 shows the phase contrast MTF curves as the shear distance S is varied from $1.5\lambda/NA$ to $0.15\lambda/NA$ (Patent Document 3 gives a detailed description of the method for computing the phase contrast MTF in the differential interference viewing method). In FIG. 6, on the horizontal axis f/f0, the spatial frequency f is normalized by the reference frequency $f0=NA/\lambda$ specified by the numerical aperture NA of the objective, and the vertical axis indicates the contrast HIT for the phase object at each frequency.

It is apparent from FIG. 6 that the phase contrast MTF curves in the differential interference viewing method show larger contrast values than the incoherent MTF curve. It is also apparent from FIG. 6 that the phase contrast MTF has a negative value when the shear distance S is large (e.g., $1.5\lambda/NA$), and this negative value indicates a state referred to as spurious resolution, in which black and white are inverted. A state in which spurious resolution does not occur, i.e., a state in which the phase contrast MTF is not negative, is generally considered to be preferable in viewing by the differential interference viewing method.

Therefore, the limits of a low spatial frequency band (region in which the value of the horizontal axis f/f0 is small) that satisfies a condition whereby the phase contrast MTF value is not negative will first be described. It is apparent from FIG. 6 that the maximum shear distance S of the low spatial frequency band is approximately $0.61\lambda/NA$ to $0.5\lambda/NA$, and these values correspond precisely with the point resolving power or line resolving power of the microscope optical system. The curve for a shear distance S of $0.61\lambda/NA$ in FIG. 6 shows that the contrast values are high in the low spatial frequency band, but that the contrast value is about 0.1 in the vicinity of horizontal axis f/f0=1.4 in the high spatial frequency band, corresponding precisely with the limit of visibility. The maximum value of the shear distance S of the objective in the present embodiment is thus $0.61\lambda/NA$, at which the point resolving power can be maintained. A more preferred maximum value for the shear distance S is $0.5\lambda/NA$, (which is closer to the incoherent MTF curve than the curve for $0.61\lambda/NA$,) at which the line resolving power can be maintained.

The limits of the high spatial frequency band (region in which the value of the horizontal axis f/f0 is large) that satisfies the condition whereby the phase contrast MTF is not negative will next be described. It is apparent from FIG. 6 that the maximum shear distance S of the high spatial frequency band corresponds to the curve having the highest contrast in the vicinity of horizontal axis f/f0=1.6, i.e., the curve for 0.3λ/NA. In this instance, instead of sacrificing contrast in the low spatial frequency band to a certain degree, the visibility in the high spatial frequency band can be kept at 0.1, which is substantially equal to the contrast value of the incoherent MTF. When the shear distance S is further reduced, contrast decreases in the low spatial frequency band as well as in the high spatial frequency band, and is unsuitable for the purposes of the present embodiment. The minimum value of the shear distance S for the objective in the present embodiment is thus 0.3λ/NA.

In summary, by setting a shear distance S that satisfies Conditional Expression (3), i.e., 0.3λ/NA≦S≦0.61λ/NA, and more preferably 0.3λ/NA≦S≦0.5λ/NA, vacuoles in the sperm head can be visualized with high contrast and with almost no compromise to the resolving power of the objective in a differential interference viewing method.

The second objective (high-magnification objective) according to the present embodiment preferably has a correction ring for correcting aberration fluctuation due to changes in temperature, cover glass thickness, and other factors. This is because the use of a correction ring makes it possible to eliminate aberration caused by temperature, error in the cover glass thickness, and other factors; and to make adjustments so that the resolution and contrast of the objective are both maximized.

EXAMPLES

Examples of the second objective (dry-type high-magnification objective) according to the present embodiment will be described.

First Example

Figure 7:
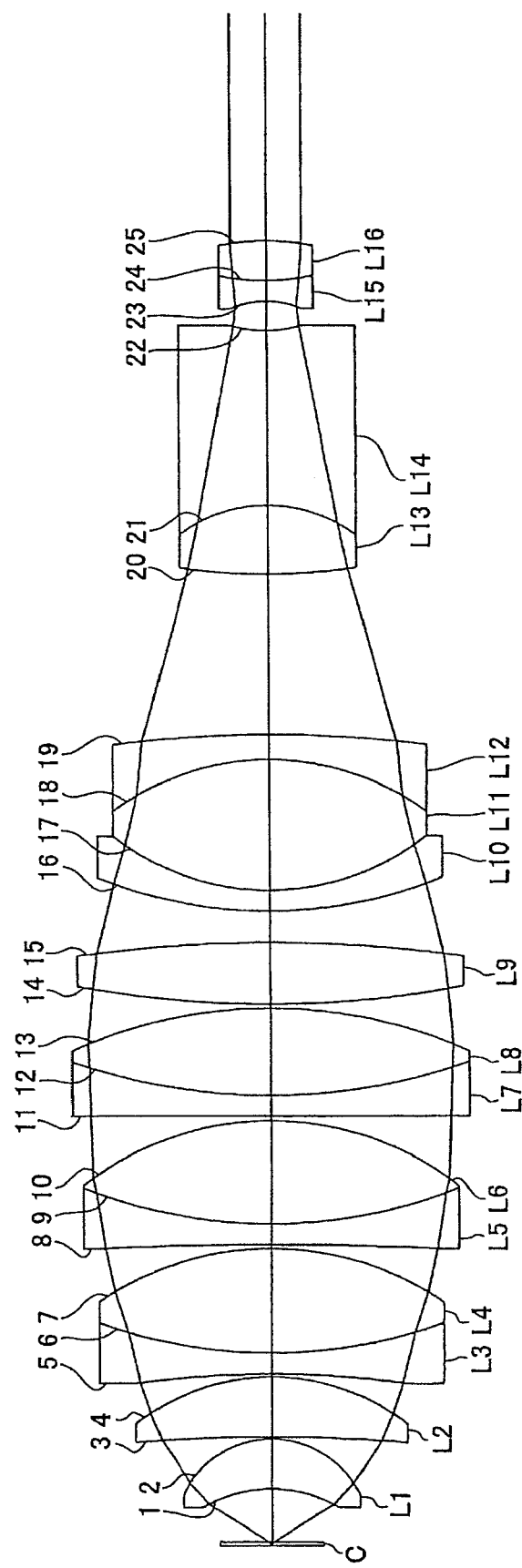
FIG. 7 is a sectional view showing the structure of the second objective (dry-type high-magnification objective) according to a first example.

A first example will be described using FIG. 7, FIG. 8, and Table 1. FIG. 7 is a sectional view showing the lens structure of the second objective (dry-type high-magnification lens) according to the present example. As shown in FIG. 7, the microscope objective in the present example comprises, in order from the object, a positive meniscus lens L1 having a concave surface facing the object; a positive meniscus lens L2 having a concave surface facing the object; a cemented lens composed of a double-concave lens L3 and a double-convex lens L4; a cemented lens composed of a double-concave lens L5 and a double-convex lens L6; a cemented lens composed of a planoconcave lens L7 and a double-convex lens L8; a double-convex lens L9; a cemented lens composed of a negative meniscus lens L10 having a convex surface facing the object, a double-convex lens L11, and a negative meniscus lens L12 having a concave surface facing the object; a cemented lens composed of a double-convex lens L13 and a double-concave lens L14; and a cemented lens composed of a double-concave lens L15 and a double-convex lens L16. A cover glass C is provided on the object side of the positive meniscus lens L1.

Table 1 shows the various values of the lenses that constitute the second objective of the present example. In the various entries shown in Table 1, m represents the order of lens surfaces (hereinafter referred to as surface numbers) from the object along the direction of travel of a ray of light, r represents the radius of curvature of each lens, d represents the distance on the optical axis from each optical surface to the next optical surface (or image surface), nd represents the refractive index with respect to the d-line (wavelength: 587.6 nm), and vd represents the Abbe number based on the d-line. Surface numbers 1 through 25 in Table 1 correspond to surfaces 1 through 25 shown in FIG. 7. In the table, β represents the magnification, WD represents the working distance, and NA represents the numerical aperture.

In the table, the radius of curvature r, the distance d to the next lens surface, and other lengths are generally represented in millimeter units. However, since equivalent optical performance is obtained whether in proportional magnification or proportional reduction in the optical system, the units are not limited to millimeters; other appropriate units may be used. The value "∞" for the radius of curvature in the table indicates a plane, and the refractive index of "1.00000" for air is not noted.

TABLE 1

Lens data
β = 100, WD = 1.4, NA = 0.85

| m | r | d | nd | vd |
|---|---|---|---|---|
|  | ∞ | 0.17000 | 1.52216 | 58.80 (cover glass C) |
|  | ∞ | 2.50462 |  |  |
| 1 | −6.47161 | 2.37000 | 1.81600 | 46.621 |
| 2 | −4.72849 | 0.10000 |  |  |
| 3 | −83.0402 | 2.83000 | 1.49782 | 82.557 |
| 4 | −10.6607 | 0.15000 |  |  |
| 5 | −46.5266 | 1.00000 | 1.61340 | 44.266 |
| 6 | 24.27074 | 4.95000 | 1.43385 | 95.247 |
| 7 | −14.7782 | 0.20000 |  |  |
| 8 | −174.834 | 1.00000 | 1.61340 | 44.266 |
| 9 | 24.11495 | 4.95000 | 1.43385 | 95.247 |
| 10 | −14.5394 | 0.20000 |  |  |
| 11 | ∞ | 1.00000 | 1.61340 | 44.266 |
| 12 | 28.67355 | 4.20000 | 1.43385 | 95.247 |
| 13 | −23.0153 | 0.20000 |  |  |
| 14 | 48.93548 | 3.00000 | 1.49782 | 82.557 |
| 15 | −65.8669 | 1.52002 |  |  |
| 16 | 21.78198 | 1.00000 | 1.72916 | 54.660 |
| 17 | 11.99437 | 6.30000 | 1.49782 | 82.557 |
| 18 | −12.5334 | 1.20000 | 1.75500 | 52.318 |
| 19 | −59.9845 | 7.75003 |  |  |
| 20 | 27.89895 | 3.35000 | 1.59240 | 68.328 |
| 21 | −7.03528 | 8.40000 | 1.65412 | 39.682 |
| 22 | 5.87805 | 1.40000 |  |  |
| 23 | −4.44814 | 1.00000 | 1.80440 | 39.567 |
| 24 | 11.0118 | 1.90000 | 1.92286 | 18.896 |
| 25 | −11.4804 |  |  |  |

FIG. 8 shows several aberration diagrams for the microscope objective according to the present example, wherein FIG. 8A is a spherical aberration diagram, FIG. 8B is an astigmatism diagram, and FIG. 8C is a distortion diagram. In FIG. 8, NA is the numerical aperture, y is the image height (mm), the solid line is the d-line (wavelength: 587.6 nm), the dashed line is the C-line (wavelength: 656.3 nm), the single-dashed line is the F-line (wavelength: 486.1 nm), and the double-dashed line is the g-line (wavelength 435.8 nm). In the astigmatism diagram, the solid line represents the sagittal image surface, and the dashed line represents the meridional image surface.

As is apparent from the aberration diagrams shown in FIG. 8, aberrations are satisfactory corrected, and excellent imaging performance is maintained in the second objective (dry-type high-magnification objective) according to the present example.

As described above, according to the present invention, there is provided a microscope system suitable for IMSI/ICSI, whereby it is possible to accurately and rapidly perform the sequence of operations in which the presence of vacuoles in a sperm head and other characteristics are viewed by a differential interference viewing method using a dry-type high-magnification (60 or higher and 100 or lower) objective to select a sperm, whereupon the objectives are exchanged through the use of the turret 16 or the like, and the selected sperm is injected into an ovum while viewed by a differential interference viewing method or modulation contrast viewing method using a medium-magnification (20 or higher and 40 or lower) objective, which is also a dry-type objective.

The essential characteristics of embodiments were described above to aid in understanding the present invention, but the present invention shall not be construed as being limited to the embodiments described above.

What is claimed is:

1. A microscopic insemination viewing method characterized in comprising, in sequence:
    a first step of visually observing and selecting a sperm by a differential interference viewing method using a dry objective having a magnification of from 60 or higher to 100 or lower; and
    a second step of visually observing an ovum and the selected sperm by any one of a differential interference viewing method and a modulation contrast viewing method using a dry objective having a magnification of from 20 or higher to 40 or lower, and injecting the selected sperm into the ovum.

2. The microscopic insemination viewing method according to claim 1, characterized in that the following conditional expressions are satisfied:

$$0.78 \leq NA < 1.0$$

$$f/3 \leq WD < 2f,$$

where NA is the numerical aperture of the dry objective having a magnification of from 60 or higher to 100 or lower, f is focal length thereof, and WD is working distance thereof.

3. The microscopic insemination viewing method according to claim 1, characterized in that the following conditional expression is satisfied when viewing by the differential interference viewing method using the dry objective having a magnification of from 60 or higher to 100 or lower:

$$0.3\lambda/NA \leq S \leq 0.61\lambda/NA,$$

where S is the shear distance in the object plane, NA is the numerical aperture of the dry objective having a magnification of from 60 or higher to 100 or lower, and $\lambda$ is the wavelength of the viewed light.

4. The microscopic insemination viewing method according to claim 1, characterized in that the dry objective having a magnification of from 60 or higher to 100 or lower has a correction ring for correcting aberration fluctuation due to changes in factors including temperature and cover glass thickness.

* * * * *